United States Patent
Shimada

(10) Patent No.: US 10,632,291 B2
(45) Date of Patent: Apr. 28, 2020

(54) MEDICAL ELONGATED BODY

(71) Applicant: TERUMO KABUSHIKI KAISHA, Shibuya-ku, Tokyo (JP)

(72) Inventor: Daisuke Shimada, Shizuoka (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 406 days.

(21) Appl. No.: 15/391,008

(22) Filed: Dec. 27, 2016

(65) Prior Publication Data
US 2017/0197065 A1 Jul. 13, 2017

(30) Foreign Application Priority Data
Jan. 12, 2016 (JP) .................................. 2016-003872

(51) Int. Cl.
*A61M 25/10* (2013.01)
*A61M 25/00* (2006.01)

(52) U.S. Cl.
CPC .... *A61M 25/1002* (2013.01); *A61M 25/0026* (2013.01); *A61M 25/104* (2013.01); *A61M 25/0009* (2013.01); *A61M 2025/0004* (2013.01); *A61M 2025/0008* (2013.01); *A61M 2210/105* (2013.01); *A61M 2210/1032* (2013.01); *A61M 2210/1042* (2013.01); *A61M 2210/1089* (2013.01); *A61M 2210/12* (2013.01)

(58) Field of Classification Search
CPC .. A61M 2025/0004; A61M 2025/0008; A61M 2210/1032; A61M 2210/1042; A61M 2210/105; A61M 2210/1089; A61M 2210/12; A61M 25/0009; A61M 25/0026; A61M 25/1002; A61M 25/104
See application file for complete search history.

(56) References Cited

U.S. PATENT DOCUMENTS

| | | | | |
|---|---|---|---|---|
| 3,094,124 A | * | 6/1963 | Birtwell | A61M 25/00 604/523 |
| 2016/0113482 A1 | * | 4/2016 | Ushijima | A61B 1/00193 600/111 |

FOREIGN PATENT DOCUMENTS

| | | |
|---|---|---|
| JP | 2013-116329 A | 6/2013 |
| WO | WO 2007/076324 A2 | 7/2007 |

* cited by examiner

*Primary Examiner* — Ryan J. Severson
*Assistant Examiner* — Mohamed G Gabr
(74) *Attorney, Agent, or Firm* — Buchanan Ingersoll & Rooney PC

(57) ABSTRACT

A medical elongated body including a catheter main body. The catheter main body has a tubular body and a lumen. The tubular body includes a guide wire lumen into which a guide wire is insertable. The tubular body also a distal member positioned at the distal portion of the tubular body. The distal member has a lumen that communicates with the guide wire lumen. The inner diameter of the distal member decreases between the proximal end and a distal end opening of the distal member. The medical elongated body also includes a visible marker that extends circumferentially on the outer surface of the distal member to indicate a position of the distal member in the axial direction corresponding to a predetermined inner diameter of the distal member. The visible marker is visible before the medical elongated body is inserted into a living body.

13 Claims, 6 Drawing Sheets

MEDICAL ELONGATED BODY

CROSS-REFERENCES TO RELATED APPLICATIONS

This application claims priority to Japanese Patent Application No. 2016-003872 filed on Jan. 12, 2016, the entire content of which is incorporated herein by reference.

TECHNICAL FIELD

The present invention relates to a medical elongated body.

BACKGROUND ART

A medical instrument including a catheter main body consisting of an elongated tube shaped body is used when performing various kinds of medical treatment in a lesion area generated in a biological lumen of a living body. For example, a medical elongated body such as a balloon catheter which performs treatment of widening a stenosed site generated in a biological lumen is generally known as this kind of medical instrument.

In general, the medical elongated body is delivered to the lesion area generated in the biological lumen by moving along a guide wire which has been previously introduced into the biological lumen. The medical elongated body has a tube body and includes a guide wire lumen for inserting a guide wire to be maneuvered in this manner. For example, refer to the disclosure in Japanese Patent Application No. 2013-116329.

SUMMARY OF INVENTION

When making the medical elongated body travel on (i.e., move along or pass over) the guide wire, if the inner diameter of the tube body of the medical elongated body is too large with respect to the outer diameter of the guide wire, the clearance between the guide wire and the tube body is increased (i.e., the clearance is too large) and the followability (i.e., maneuverability) of a distal portion of the tube body with respect to the guide wire deteriorates. When moving the medical elongated body within a curved biological lumen, for example, there is a possibility that the distal portion of the tube body may not follow the guide wire and may unintentionally come into contact with an inner wall of the biological lumen even if the guide wire follows the shape of the biological lumen when the clearance between the guide wire and the tube body is too large. If the inner diameter of the tube body is too small with respect to the outer diameter of the guide wire, it is impossible to insert the guide wire into the tube body.

Accordingly, a medical elongated body is used that has a tube body possessing an inner diameter suitable for the outer diameter of a guide wire which has been introduced into a living body when performing various kinds of medical treatment in a lesion area generated in a biological lumen. In a case where there is a possibility that a plurality of guide wires having different outer diameters are used, it becomes necessary to prepare a plurality of medical elongated bodies suitable for the respective outer diameters of the plurality of guide wires. Preparing multiple medical elongated bodies is not economical.

The medical elongated body disclosed in this application addresses the above-described problem by allowing the insertion of a plurality of guide wires having different outer diameters. The medical elongated body also renders it is possible to favorably maintain followability (i.e., maneuverability) with respect to the guide wires.

A medical elongated body according to the present invention includes a catheter main body having a lumen. The catheter main body has a tube body including a guide wire lumen into which a guide wire is inserted, and a distal member which is disposed at a distal portion of the tube body and includes a distal opening portion and a lumen communicating with the guide wire lumen. The distal member has an outer surface and an inner surface which forms the lumen of the distal member. The lumen of the distal member becomes smaller toward a distal end from a proximal end of the distal member. The medical elongated body includes a marker portion which is visible and indicates a position on the distal member in a circumferential direction is provided on an outer surface of the distal member on a proximal side of the distal opening portion.

According to the medical elongated body disclosed here, the lumen of the distal member becomes smaller toward a proximal end from a distal end of the distal member. The marker portion (which is visible and indicates a position on the distal member in a circumferential direction) is provided further toward a proximal side than the distal opening portion. Based on this configuration, if the distal member is cut in the circumferential direction along the marker portion, an inner diameter of a distal end of the distal member after the cutting becomes a size suitable for a guide wire having an outer diameter larger than that of a guide wire which is suitable for an inner diameter (a diameter of a distal opening portion) of a distal end of the distal member before the cutting. Accordingly, it is possible to provide a medical elongated body into which it is possible to insert a plurality of guide wires having different outer diameters and in which it is possible to favorably maintain followability (i.e., maneuverability) with respect to the guide wires.

BRIEF DESCRIPTION OF THE DRAWINGS

FIG. 1(A) is a schematic view showing an overall configuration of the catheter, FIG. 1(B) is an enlarged sectional view showing a distal portion of the catheter, and FIG. 1(C) is an enlarged sectional view showing a proximal portion of the catheter.

FIG. 4(A) is a view showing a guide wire, which is comparatively thin, about to be pushed into a stenosed site within a blood vessel, FIG. 4(B) is a view showing a guide wire, which is comparatively thick, being inserted into the stenosed site within the blood vessel, FIG. 4(C) is a view showing the balloon catheter moving within a curved blood vessel, and FIG. 4(D) is a view showing a dilation portion of the balloon catheter in a dilated state within the stenosed site.

DETAILED DESCRIPTION

Set forth below is a detailed description of embodiments with reference to the drawings of a medical elongated body and a method for using a medical elongated body representing examples of the inventive medical elongated body and method disclosed here. Note that the following description does not limit the technical scope or the meaning of terms described in claims. In addition, dimensional ratios in each drawing may be exaggerated and may be different from the actual ratios for the convenience of description.

First Embodiment

Figure 1A:
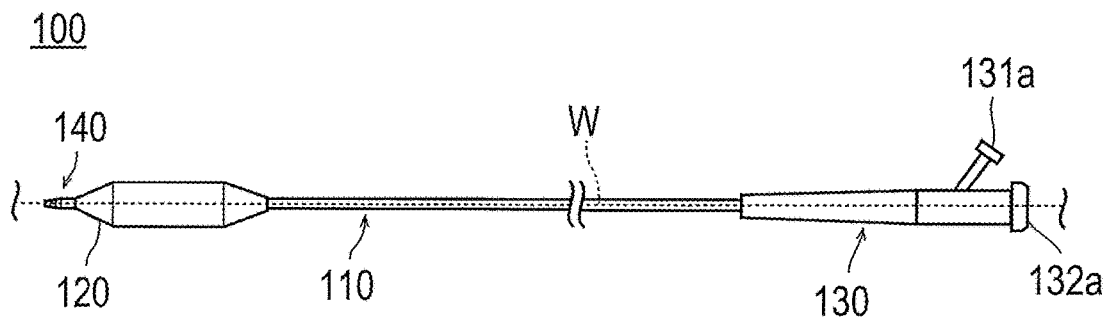
FIGS. 1(A)-1(C) are views showing a balloon catheter according to a first embodiment.
Figure 1B:
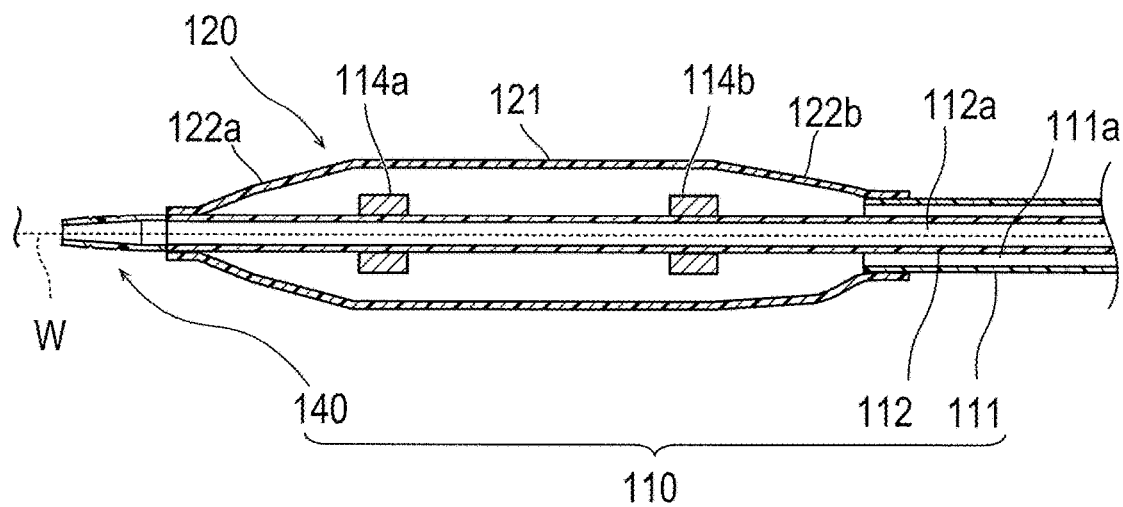
Figure 1C:
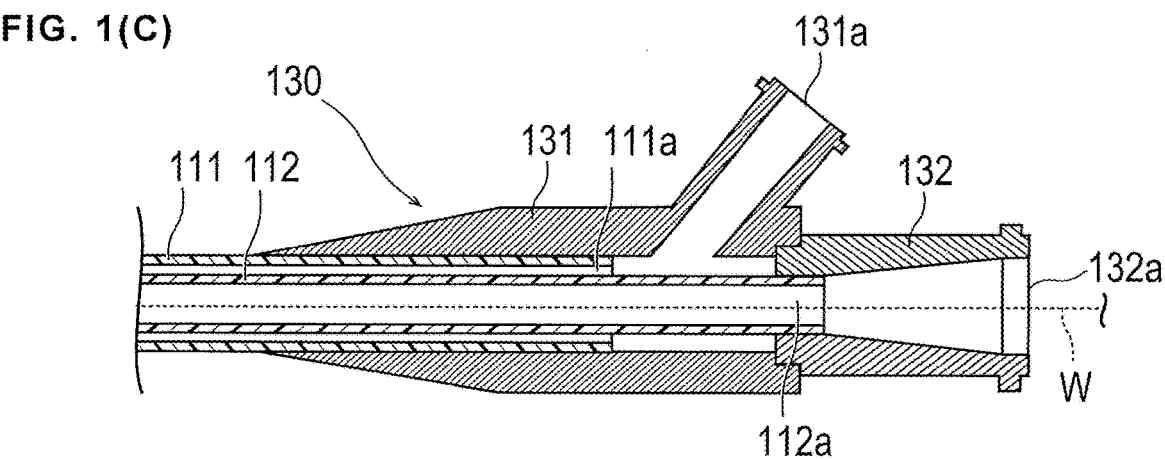

A balloon catheter 100 (corresponding to a "medical elongated body") according to the present embodiment will be described with reference to FIGS. 1(A) to 4(D). FIGS. 1(A)-1(C) is a schematic view showing the balloon catheter 100 according to the present embodiment. FIGS. 2 and 3(A)-3(D) are schematic views showing a distal member 140 of the balloon catheter 100 illustrated in FIGS. 1(A)-1(C). FIGS. 4(A)-4(D) are schematic views showing an example of using the balloon catheter 100 illustrated in FIG. 1(A). Note that FIGS. 1(A) and 1(B) simply show the shape of a dilation portion 120 in a deflated state, and the dilation portion 120 is actually folded over the outer circumference of an inner tube 112 of a shaft 110.

The balloon catheter 100 in the embodiment illustrated in FIG. 1(A) is a medical instrument for treating a stenosed site generated in a blood vessel of a lower limb. The stenosed site is treated by widening the stenosed site. However, the balloon catheter 100 is not limited to treating a stenosed site in a blood vessel of the lower limb. The balloon catheter 100 can be a medical instrument for treating a stenosed site generated in other blood vessels, bile ducts, the trachea, the esophagus, the urethra, or other biological lumens by widening the stenosed site. In addition, the balloon catheter 100 can be a medical elongated body for delivering a stent to expand the stent and indwell the stent in the stenosed site of a biological lumen.

As shown in FIG. 1(A), the balloon catheter 100 includes a flexible elongated shaft 110 (corresponding to a "catheter main body"); the dilation portion 120 which is provided on a distal side of the shaft 110 and is capable of dilating and deflating when a fluid is introduced into or discharged from the dilation portion; and a hub 130 fixed to a proximal end of the shaft 110.

Note that, in the description of this specification, an extending direction of the shaft 110 is referred to as an axial direction. In the axial direction, the side of the balloon catheter that is inserted into a biological lumen is referred to as a "distal side" or "distal end" and the side operated by a user on which the hub 130 is provided is referred to as a "proximal side" or "proximal end". In addition, a "distal portion" means a certain range including the distal end (i.e., the distal-most end) and the periphery thereof (i.e., a portion adjacent to the distal end), and a "proximal portion" means a certain range including the proximal end (i.e., the proximal-most end) and the periphery thereof (i.e., a portion adjacent to the proximal end).

As shown in FIGS. 1(B) and 1(C), the shaft 110 includes an outer tube 111. The outer tube 111 is a tube shaped body and has an open distal end and an open proximal end. The shaft 110 also includes an inner tube 112 (corresponding to a "tube body") which is a tube shaped body (i.e., an elongated cylinder) that has an open distal end and an open proximal end. The inner tube 112 is disposed in a lumen of the outer tube 111. The shaft includes the distal member 140 which is disposed at a distal portion of the inner tube 112.

A dilation lumen 111a through which a dilation fluid for dilating (i.e., expanding) the dilation portion 120 (i.e., an expansion portion) flows is formed between the outer peripheral surface of the inner tube 112 and the inner peripheral surface of the outer tube 111. As shown in FIG. 1(C), the dilation lumen 111a communicates with an injection port 131a of the hub 130 to be described below. The fluid injected into the dilation lumen 111a may be gas or a liquid. For example, the fluid may be a gas such as air, helium gas, $CO_2$ gas, or $O_2$ gas, or a liquid such as physiological salt solution or a contrast agent.

As shown in FIG. 1(B), the inner tube 112 includes a guide wire lumen 112a through which the guide wire W is inserted. As shown in FIG. 1(C), the guide wire lumen 112a communicates with a proximal opening portion 132a of the hub 130 which will be described below.

The balloon catheter 100 of the embodiment illustrated in FIG. 1(A) is a so-called over-the-wire catheter in which the guide wire W is inserted through the proximal opening portion 132a of the hub 130 and through the distal opening portion 141a of the distal member 140. However, the balloon catheter 100 may instead be configured to be a so-called rapid-exchange catheter in which an opening portion communicating with the inner tube 112 is provided between the distal side and the proximal side of the shaft 110 and the guide wire W is inserted through the opening portion and the distal opening portion 141a.

The distal portion of the inner tube 112 penetrates the inside of the dilation portion 120 as shown in FIG. 1(B). Imaging markers 114a and 114b are installed in a portion which becomes a boundary between a cylindrical portion 121 of the dilation portion 120 and a distal side tapered portion 122a, and a portion which becomes a boundary between the cylindrical portion 121 of the dilation portion 120 and a proximal side tapered portion 122b, in the inner tube 112. In other words, the imaging markers 114a and 114b are on the outer surface of the inner tube 112, at a position within the dilation portion 120.

The outer tube 111 and the inner tube 112 are preferably made of a flexible material (i.e., a material having some degree of flexibility). The outer tube 111 and/or inner tube 112 may be, for example, polyolefin such as polyethylene, polypropylene, polybutene, ethylene-propylene copolymer, ethylene-vinyl acetate copolymer, ionomer, or a mixture of two or more of these materials, a polyvinyl chloride resin, polyamide, a polyamide elastomer, polyester, a polyester elastomer, polyurethane, fluororesin, or the like.

The distal member 140 has a function of adjusting (i.e., is configured to adjust) the diameter of the lumen through which the guide wire W is inserted. The distal member 140 adjusts the diameter of the lumen in accordance with the outer diameter of the guide wire W.

Figure 2:
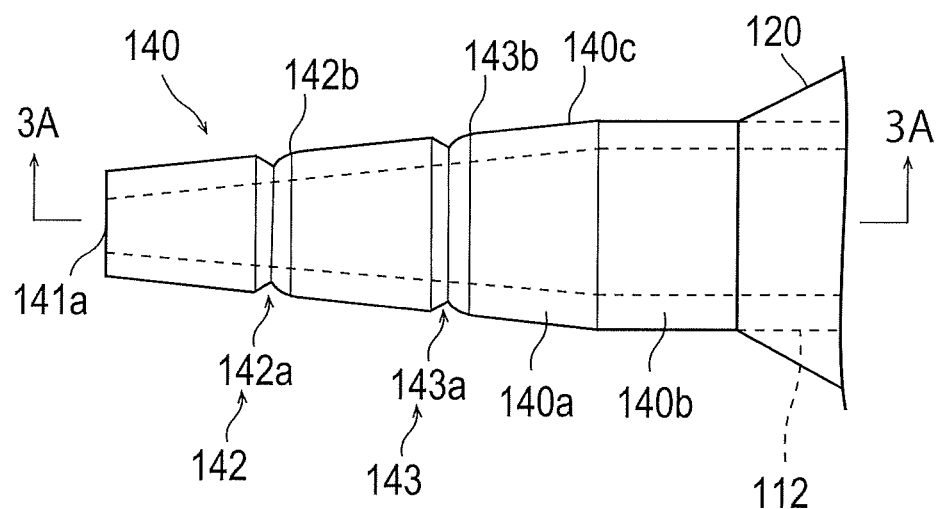
FIG. 2 is an enlarged plan view showing a distal member of the balloon catheter according to the first embodiment.
Figure 3A:
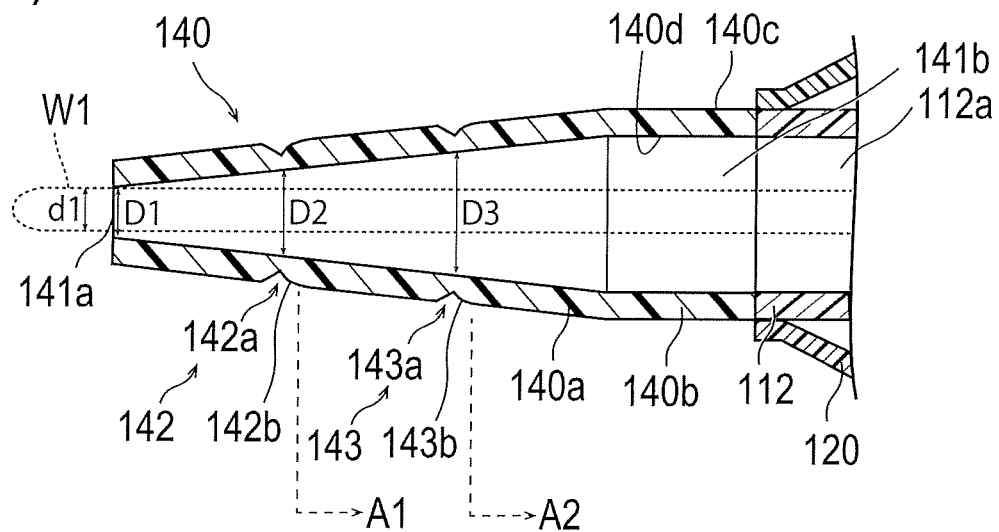
FIG. 3(A) is a cross-sectional view taken along 3A-3A line of FIG. 2.

As shown in FIGS. 2 and 3(A), the distal member 140 is a tube shaped body possessing an open distal end and an open proximal end. Hereinafter, the open portion of the distal end of the distal member 140 is referred to as the distal opening portion 141a.

As shown in FIG. 3(A), the proximal end of the distal member 140 is fixed to the distal end of the inner tube 112. Accordingly, a lumen 141b of the distal member 140 communicates with the guide wire lumen 112a of the inner tube 112. Note that the fixation position on the distal member 140 is not particularly limited as long as the proximal portion of the distal member 140 is fixed to the distal portion of the inner tube 112. For example, the proximal portion of the distal member 140 may be fixed to the distal portion of the inner tube 112 such that the proximal portion of the distal member overlaps the distal portion of the inner tube by a certain degree of length in the axial direction. In addition, the fixation method is not particularly limited. It is possible to use, for example, a method such as welding or adhesion using an adhesive.

The distal member 140 includes a tapered portion 140a. The outer diameter of the tapered portion 140a decreases between the distal end and the proximal end (i.e., the tapered portion 140a has a larger inner diameter at the proximal end than at the distal end). The distal member 140 also includes a flat portion 140b which is continuous to the proximal side of the tapered portion 140a and has a substantially constant outer diameter in the extending direction (i.e., the axial direction or the horizontal direction in the drawing) of the distal member 140.

The inner diameter of the tapered portion 140a decreases toward the distal end from the proximal end. That is, in the distal member 140, the lumen 141b in a portion in which the tapered portion 140a is provided becomes smaller toward the distal end from the proximal end. In other words, the inner diameter of the distal member decreases between the proximal end of the distal member and the distal end opening so that the lumen of the distal member narrows in a direction toward the distal end opening of the distal member. The inner diameter of the flat portion 140b is substantially constant toward the distal end from the proximal end, and is the same as the inner diameter of the proximal end of the tapered portion 140a.

As shown in FIGS. 2 and 3(A), a first marker portion 142 and a second marker portion 143 are provided in the outer surface 140c of the distal member 140. The first and second marker portions 142, 143 indicate the position on the distal member around the circumferential direction (i.e., the first and second marker portions 142, 143 extend around the outer surface 140c of the distal member 140 in the circumferential direction to indicate an axial position).

The first marker portion 142 and the second marker portion 143 have a function of indicating (i.e., are configured to indicate) a cutting position when cutting the distal member 140 in the circumferential direction. This cutting position indication signals to a user that the inner diameter of the distal member 140 is sized suitably for the outer diameter of a predetermined guide wire (i.e., a guide wire having a specific predetermined outer diameter). A cutting tool used for cutting the distal member 140 is not particularly limited as long as it can cut the distal member 140. Cutting tool examples for cutting the distal member 140 include scissors, a scalpel, and a knife which may be used in medical sites.

The marker portions 142 and 143 are each provided on the outer surface of the tapered portion 140a proximal to the distal opening portion 141a. The second marker portion 143 is provided proximal to the first marker portion 142.

The first marker portion 142 is formed by a first groove portion 142a. The first groove portion 142a is recessed from the outer surface 140c side toward the inner surface 140d side of the distal member 140. Similarly, the second marker portion 143 is formed by a second groove portion 143a which is recessed from the outer surface 140c side toward the inner surface 140d side of the distal member 140. As shown in FIG. 2, each of the groove portions 142a and 143a is formed in an annular shape along the circumferential direction (e.g., the groove portions 142a and 143a extend 360° around the outer circumferential surface of the distal member 140). As shown in FIG. 3(A), each of the groove portions 142a and 143a becomes smaller toward the inner surface 140d side from the outer surface 140c side of the distal member 140. That is, the width (the length of the distal member 140 along the extending direction) of each of the groove portions 142a and 143a decreases from the outer surface 140c side toward the inner surface 140d side. Note that, in the embodiment illustrated in FIG. 2, each of the groove portions 142a and 143a has a substantially V-shape in a cross section taken along the extending direction of the distal member 140. However, the shape of the each of the groove portions 142a and 143a is not particularly limited as long as the groove portions are recessed from the outer surface 140c side toward the inner surface 140d side of the distal member 140. For example, each of the groove portions 142a and 143a may have a U-shape in the cross section taken along the extending direction of the distal member 140.

Figure 3B:
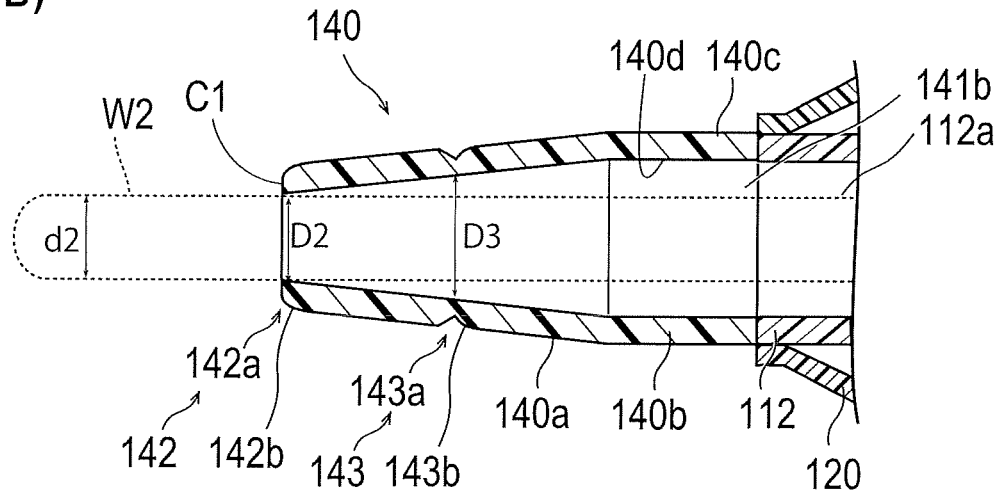
FIG. 3(B) is a view showing a state in which the distal member is cut at a first marker portion.

In addition, a first curved portion 142b is formed on the outer surface 140c of the distal member 140. The first curved portion 142b is a portion in which a space between the first groove portion 142a and a portion A1 on the proximal side of the first groove portion 142a is rounded. Similarly, a second curved portion 143b is formed on the outer surface 140c of the distal member 140. The second curved portion 143b is a portion in which a space between the second groove portion 143a and a portion A2 on the proximal side of the second groove portion 143a on the outer surface 140c of the distal member 140 is rounded. In other words, the outer surface at the proximal portion of the groove portions 142a, 143a may be a rounded portion 142b, 143b as illustrated in FIGS. 3(A) and 3(B).

The diameter of the distal opening portion 141a of the distal member 140 is referred to as D1. The inner diameter of the distal member 140 at a position at which the first marker portion 142 (in particular, a portion which is most deeply recessed to the inner surface 140d side of the first groove portion 142a) on the distal side is provided is referred to as D2. The inner diameter of the distal member 140 at a position at which the second marker portion 143 (in particular, a portion which is most deeply recessed on the inner surface 140d side of the second groove portion 143a) on the proximal side is provided is referred to as D3.

The diameter D1 of the distal opening portion 141a and the inner diameters D2 and D3 of the distal member 140 can be respectively set to become a size suitable for the outer diameter of a predetermined guide wire.

In the present embodiment, the diameter D1 of the distal opening portion 141a of the distal member 140 has a size suitable for a guide wire W1 having an outer diameter d1. The inner diameter D2 of the distal member 140 has a size suitable for a guide wire W2 having an outer diameter d2. The outer diameter d2 of the second guide wire W2 is larger than the outer diameter d1 of the first guide wire W1. The inner diameter D3 of the distal member 140 has a size suitable for a guide wire W3 having an outer diameter d3, which is larger than the outer diameter d2. Note that, in the description exemplifying a relationship between the outer diameter d1 of the guide wire W1 and the diameter D1 of the distal opening portion 141a in the specification, a "size suitable for the guide wire" indicates that the clearance between the outer diameter d1 of the guide wire W1 and the diameter D1 of the distal opening portion is within a range in which it is possible to smoothly move the distal member 140 forward and backward with respect to the guide wire W1 in the axial direction and is also within a range in which it is possible to favorably maintain followability (i.e., maneuverability) with respect to the guide wire W1.

The distal member 140 is preferably made of a flexible material (or at least flexible to some extent) and a material that is capable of being cut by a cutting tool. The distal member 140 material may be, for example, polyolefin such as polyethylene, polypropylene, polybutene, ethylene-propylene copolymer, ethylene-vinyl acetate copolymer, ionomer, or a mixture of two or more of these materials, a polyvinyl chloride resin, polyamide, a polyamide elastomer, polyester, a polyester elastomer, polyurethane, fluororesin, or the like.

The dilation portion 120 widens a stenosed site (i.e., is configured to expand to widen a stenosed site).

The dilation portion 120 is folded over the outer circumference of the inner tube 112 in a deflated state. As shown in FIG. 1(B), the dilation portion 120 has a cylindrical portion 121 possessing a substantially constant outer diameter in the extending direction (i.e., the axial direction or the horizontal direction of FIG. 1(B)) of the dilation portion 120. The distal side of the cylindrical portion 121 includes a distal side tapered portion 122a. The outer diameter of the distal side tapered portion 122a decreases toward the distal side (i.e., the outer diameter at the distal end is smaller than the outer diameter at the proximal end of the distal side tapered portion 122a). The proximal side of the cylindrical portion 121 includes a proximal side tapered portion 122b. The outer diameter of the proximal side tapered portion 122b decreases toward the proximal side (i.e., the outer diameter at the proximal end is smaller than the outer diameter at the distal end of the proximal side tapered portion 122b).

The proximal portion of the dilation portion 120 is fixed to the distal portion of the outer tube 111, and the distal portion of the dilation portion 120 is fixed to the distal portion of the inner tube 112 (i.e., to the outer surface of the inner tube 112 at a distal portion of the inner tube 112). Note that the fixation position on the dilation portion 120 on the distal side is not particularly limited as long as the distal member 140 is positioned distal to the dilation portion 120. For example, the distal portion of the dilation portion 120 may be fixed to the proximal portion of the distal member 140. In other words, the dilation portion 120 and the distal member 140 may axially overlap, but at least a portion of the distal member 140 extends distally beyond the dilation portion 120.

The dilation portion 120 is preferably made of a material which is flexible to some extent. It is possible to use, for example, polyolefin such as polyethylene, polypropylene, polybutene, ethylene-propylene copolymer, ethylene-vinyl acetate copolymer, ionomer, or a mixture of two or more of these materials, a plasticized polyvinyl chloride resin, and thermoplastic resins such as polyamide, a polyamide elastomer, polyester, a polyester elastomer, polyurethane, and fluororesin, as the material of the dilation portion 120.

As shown in FIG. 1(C), the hub 130 has an outer tube hub 131 which includes an injection port 131a. The injection port 131a functions as a port for introducing and discharging a dilation fluid. The hub 130 includes an inner tube hub 132 which has a proximal opening portion 132a functioning as a port for introducing the guide wire W.

The outer tube hub 131 is fixed to the proximal portion of the outer tube 111 (i.e., to the outer surface of the outer tube 111 at a proximal portion of the outer tube 111). The fixation method is not particularly limited, but permissible fixation method examples include adhesion using an adhesive, heat-welding, and fixation using a fastener (not shown in the drawing).

The inner tube hub 132 is disposed on the proximal side of the outer tube hub 131 and is fixed to the outer tube hub 131. In addition, the inner tube hub 132 is fixed to the proximal portion of the inner tube 112. As illustrated in FIG. 1(C), for example, the outer surface of the inner tube hub 132 may be fixed to an inner surface of the outer tube hub 131, and the inner surface of the inner tube hub 132 may be fixed to the outer surface of the inner tube 112 at a proximal portion of the inner tube 112. The fixation method is not particularly limited, but permissible fixation method examples include adhesion using an adhesive, heat-welding, and fixation using a fastener (not shown in the drawing).

Examples of the hub 130 material include thermoplastic resins such as polycarbonate, polyamide, polysulfone, polyarylate, and a methacrylate-butylene-styrene copolymer.

Next, an example of the sequence of inserting the balloon catheter 100 through a stenosed site N formed in a blood vessel V1 of a lower limb will be described with reference to FIGS. 4(A)-4(B). Note the following example describes the guide wire W1 being switched to the guide wire W2 in accordance with a pushing force needed with respect to the stenosed site N.

Figure 4A:
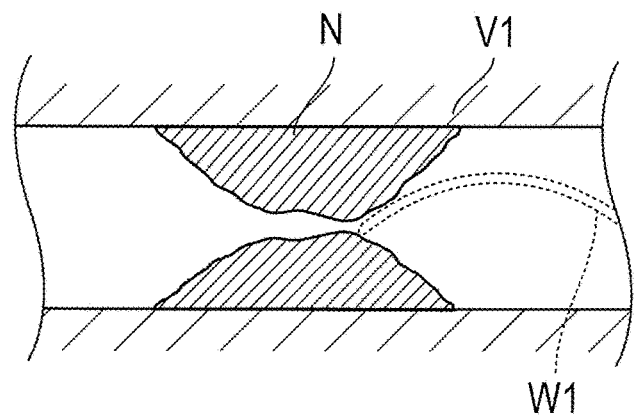
FIGS. 4(A)-4D are views showing an example of using the balloon catheter according to the first embodiment.
Figure 4B:
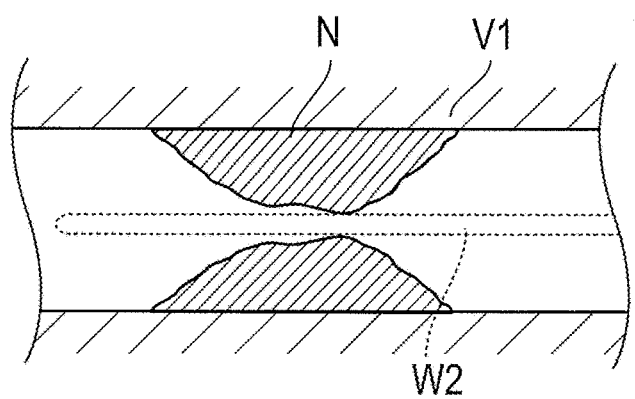

As shown in FIG. 4(A), a user first attempts to push the guide wire W1 with the outer diameter d1 to the stenosed site N.

In a case where it is impossible to push the guide wire W1 to the stenosed site N because the pushing force is insufficient due to the guide wire W1 having an outer diameter that is too thin, the guide wire W1 is removed from the inside of the living body and the guide wire W2 having a larger outer diameter d2 than the outer diameter d1 of the guide wire W1 is introduced into the living body instead of the guide wire W1. FIG. 4(B) illustrates the guide wire W2 having a larger outer diameter d2 replacing the guide wire W1 in the living body.

Next, the user cuts the distal member 140 of the balloon catheter 100 at a position where the first marker portion 142 is provided, using a cutting tool. FIG. 3(B) illustrates the distal member 140 after a cut has been made at the first marker portion 142. The inner diameter D2 of the distal member 140 at the distal end (cut surface C1) of the distal member 140 after the cutting has a size suitable for the outer diameter d2 of the guide wire W2.

Figure 3C:
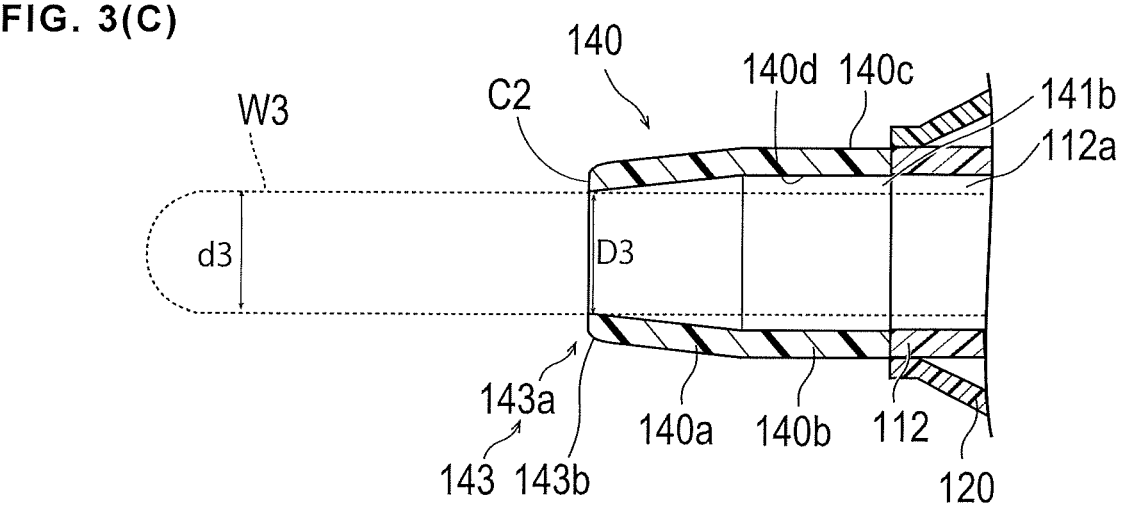
FIG. 3(C) is a view showing a state in which the distal member is cut at a second marker portion.

In a case where the guide wire W1 has been inserted through the stenosed site N, the distal member 140 of the balloon catheter 100 may be used as it is without being cut. When it is impossible to push the guide wire W2 to the stenosed site N because the pushing force is insufficient due to the guide wire W2 having too thin of an outer diameter, the guide wire W2 may be removed from the inside of the living body and the guide wire W3 having a larger outer diameter d3 than the outer diameter d2 of the guide wire W2 may be introduced into the living body. When the guide wire W3 is inserted through the stenosed site N, the user cuts the distal member 140 at a position at which the second marker portion 143 is provided. FIG. 3(C) illustrates the distal member 140 after a cut has been made at the second marker portion 143. The inner diameter D3 of the distal end (cut surface C2) of the distal member 140 after being cut as illustrated in FIG. 3(C) has a size suitable for the outer diameter d3 of the guide wire W3. It is possible to deal with (i.e., configure the distal member 140 to smoothly operate with) any of the guide wires W1, W2, and W3 if the distal member 140 of the balloon catheter 100 is cut in this manner.

Therefore, it is unnecessary to prepare a plurality of balloon catheters in accordance with the different possible sized outer diameters of a plurality of guide wires W1, W2, and W3 that can be used, and thus, the medical elongated body is excellent in economical efficiency.

The first marker portion 142 is formed by the first groove portion 142a. Therefore, a blade of a cutting tool is fitted to the first groove portion 142a during the cutting and the distal member 140 can be cut at an appropriate position. It is possible to easily obtain a cut surface which is comparatively flat and favorable based on the configuration of the first groove portion 142a because the cutting can be performed while making the blade of the cutting tool follow the first groove portion 142a. The first groove portion 142a becomes smaller toward the inner surface 140d side from the outer surface 140c side of the distal member 140. Therefore, the blade of the cutting tool is dug into the most deeply recessed portion of the groove portion. Thus, it is possible to cut the distal member 140 at a more appropriate position and to obtain a more favorable cut surface. Note that it is possible to obtain the same effect when the distal member 140 is cut at the second marker portion 143.

Figure 4C:
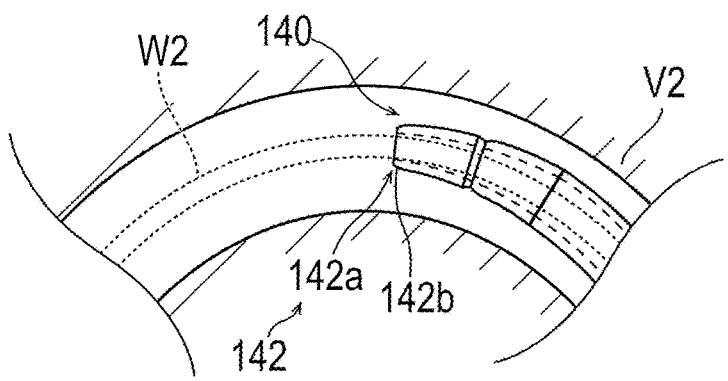

After the distal portion 140 has been cut (as needed), the user delivers the dilation portion 120 of the balloon catheter 100 to the stenosed site N by making the balloon catheter 100 travel on the guide wire W2 which has been inserted through the stenosed site N. The inner diameter D2 of the distal member 140 has a size suitable for the outer diameter d2 of the guide wire W2. Therefore, even if there is a curved blood vessel V2 in the stenosed site N as shown in FIG. 4(C), it is possible to suitably prevent the distal portion of the distal member 140 (after being cut) from coming into contact with the inner wall of the blood vessel V2. This is because the distal member 140 follows the curved guide wire W2 along the blood vessel V2.

The first curved portion 142b is formed in the periphery of the cut surface C1 when the distal member 140 is cut in the first marker portion 142. Therefore, even if the distal portion of the distal member 140 is unintentionally brought into contact with the intravascular wall, it is possible to suitably prevent any damage to the intravascular wall.

Figure 4D:
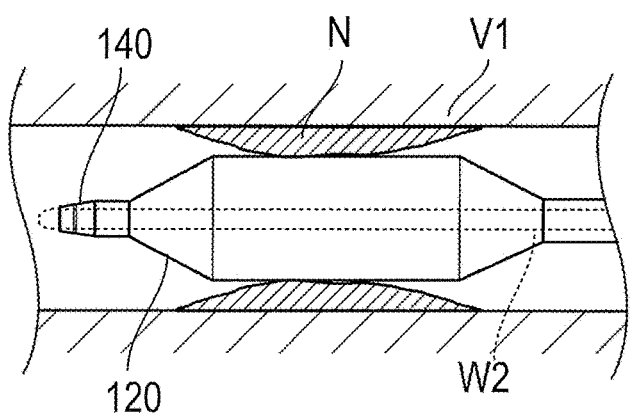

Once the balloon catheter has been appropriately maneuvered into position at the stenosed site, the user injects a fluid into the dilation lumen 111a from the injection port 131a to dilate the dilation portion 120 in the stenosed site N as shown in FIG. 4(D). Accordingly, the stenosed site N is widened.

Next, the user removes the balloon catheter 100 from the inside of the living body.

The balloon catheter 100 according to the embodiment illustrated in FIG. 1(A) includes the shaft 110 having a lumen. The shaft 110 has the inner tube 112 including the guide wire lumen 112a into which the guide wire W is inserted; and the distal member 140 which is disposed at the distal portion of the inner tube 112 and includes the distal opening portion 141a and the lumen 141b communicating with the guide wire lumen 112a. The distal member 140 has an outer surface 140c and an inner surface 140d which forms the lumen 141b of the distal member 140. The lumen 141b of the distal member 140 becomes smaller toward the distal end from the proximal end of the distal member 140. The outer surface 140c of the distal member 140 includes marker portions 142 and 143 on the proximal side of the distal opening portion 141a. The marker portions 142 and 143 are visible and extend circumferentially on the outer surface 140c to indicate an axial position of the distal member 140.

If the distal member 140 is cut in the circumferential direction along the first marker portion 142 (or the second marker portion 143), the inner diameter D2 (or D3) of the distal end of the distal member 140 after the cutting becomes a size suitable for the guide wire W2 (or W3) having the outer diameter d2 (or the outer diameter d3) larger than the outer diameter d1 of the guide wire W1 which is suitable for the inner diameter D1 (the diameter D1 of the distal opening portion 141a) of the distal end of the distal member 140 before the cutting. The balloon catheter 100 disclosed here thus makes it possible to insert a plurality of guide wires W1, W2, and W3 having different outer diameters and favorably maintain followability (i.e., maneuverability) with respect to the guide wires W1, W2, and W3.

The first marker portion 142 includes the first groove portion 142a which is recessed from the outer surface 140c side toward the inner surface 140d side of the distal member 140. The second marker portion 143 includes the second groove portion 143a which is recessed from the outer surface 140c side toward the inner surface 140d side of the distal member 140. During the cutting at one of the marker portions 142, 143, it is possible to cut at an appropriate position since a blade of a cutting tool (such as a scalpel) is fitted to the groove portion. In addition, it is possible to obtain a flat cut surface when the blade of the cutting tool follows the groove portion (i.e., the cut is made at the joint of the groove portion 142a, 143a). Therefore, it is possible to favorably maintain the shape of the distal portion of the distal member 140 after the cutting.

Each of the groove portions 142a and 143a becomes smaller toward the inner surface 140d side from the outer surface 140c side of the distal member 140. For this reason, the blade of the cutting tool is dug into the most deeply recessed portion of each of the groove portions 142a and 143a. Therefore, it is possible to perform the cutting at an appropriate position (i.e., at exactly the desired location in the axial direction). In addition, since it is possible to obtain a flatter cut surface by making the blade of the cutting tool follow the most deeply recessed portion, it is possible to more favorably maintain the shape of the distal portion of the distal member 140 after the cutting.

The distal member 140 includes the first curved portion 142b in which the space between the first groove portion 142a and the portion A1 on the proximal side of the first groove portion 142a on the outer surface 140c of the distal member 140 is rounded. The distal member 140 also includes the second curved portion 143b in which the space between the second groove portion 143a and the portion A2 on the proximal side of the second groove portion 143a on the outer surface 140c of the distal member 140 is rounded. These rounded portions 142b, 143b render it possible to suitably prevent any damage to the inner wall of the biological lumen (e.g., a blood vessel) even if the distal portion of the distal member 140 after being cut is unintentionally brought into contact with the inner wall of the biological lumen.

Modification Example of First Embodiment

Figure 5A:
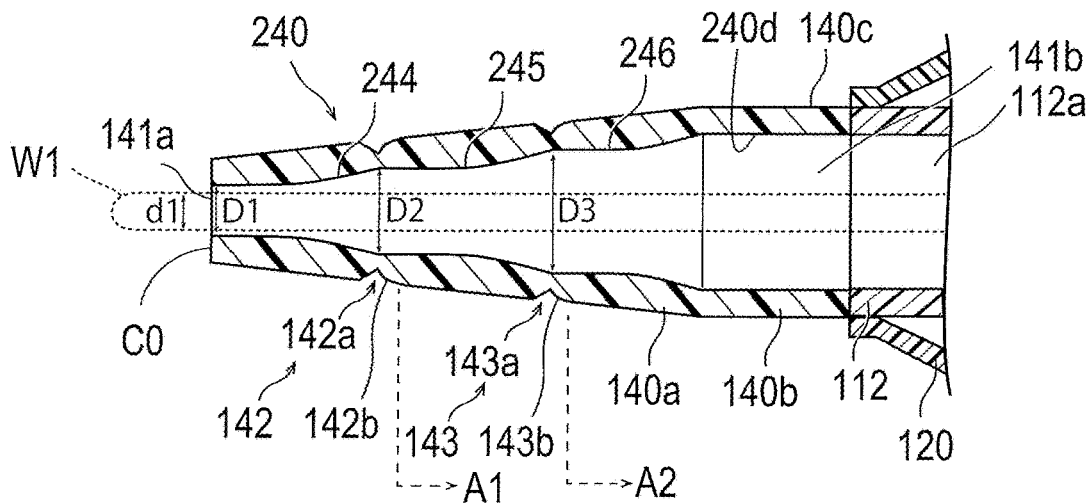
FIG. 5(A) is an enlarged sectional view showing a distal member according to a modification example of the first embodiment.
Figure 5B:
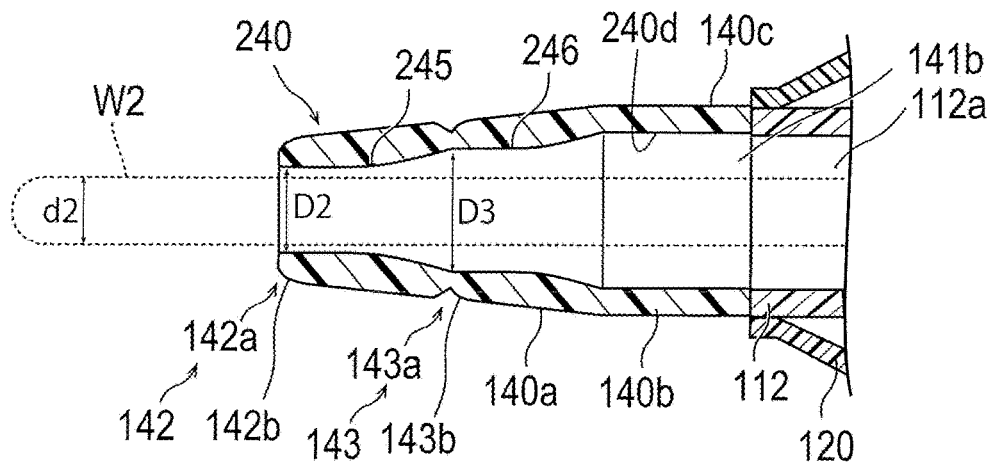
FIG. 5(B) is a view showing a state in which the distal member is cut at a first marker portion.
Figure 5C:
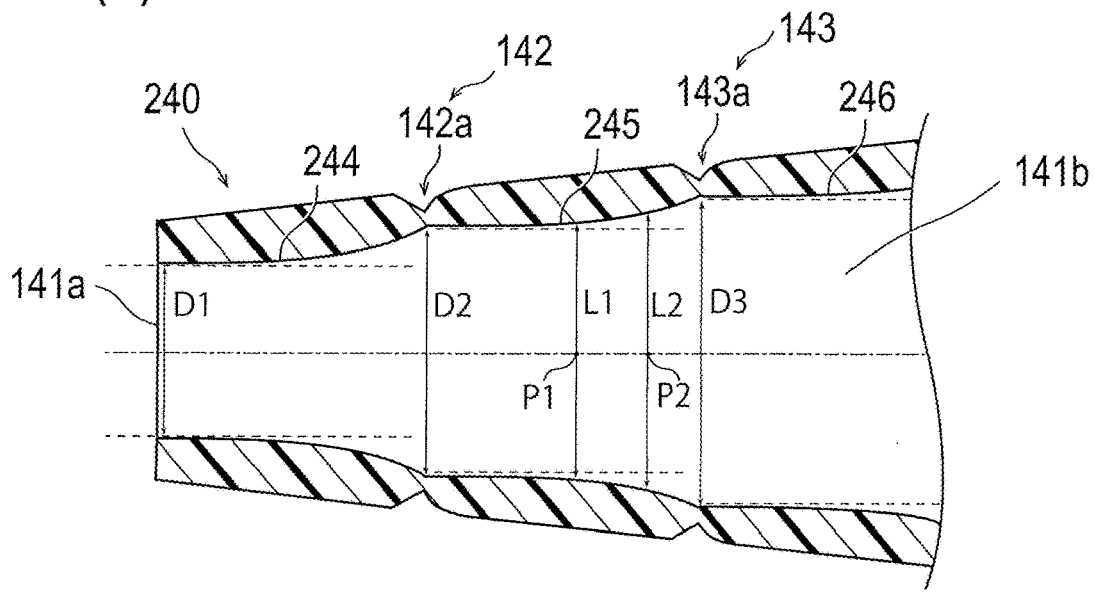
FIG. 5(C) is an enlarged view of FIG. 5(A) on a distal side.

FIGS. 5(A)-5(C) are views showing a distal member 240 according to a modification example of the first embodiment. Note that the same reference numerals will be given to the same configurations as those in the first embodiment, and the description of similar aspects of the first embodiment will not be repeated.

The distal member 240 according to the modification example of the first embodiment is different from the first embodiment because the distal member 240 includes convex portions 244, 245, and 246 protruding towards a lumen 141*b* of the distal member 240 on an inner surface 240*d* of the distal member 240 as shown in FIG. 5(A). The distal member 240 according to the modification example of the first embodiment is described in detail below.

A first convex portion 244 protruding toward the lumen 141*b* of the distal member 240 on the inner surface 240*d* of the distal member 240 is formed in the region between a distal surface C0 of the distal member 240 (i.e., the distal-most end of the distal member 240) and the first marker portion 142.

A second convex portion 245 protruding toward the lumen 141*b* of the distal member 240 on the inner surface 240*d* of the distal member 240 is formed in a region between the first marker portion 142 and a second marker portion 143 (which are adjacent to each other).

A third convex portion 246 protruding toward the lumen 141*b* of the distal member 240 on the inner surface 240*d* of the distal member 240 is formed in a region between the second marker portion 143 and a flat portion 140*b* at the proximal portion of the distal member 240.

In the embodiment illustrated in FIGS. 5(A)-5(C), each of the convex portions 244, 245, and 246 is formed in an annular shape along the circumferential direction of the distal member 240. However, it is unnecessary for each of the convex portions 244, 245, and 246 to be formed in the annular shape along the circumferential direction. Each of the convex portions 244, 245, and 246 may be partially formed in the circumferential direction.

As shown in FIG. 5(C), each of the convex portions 244, 245, and 246 is formed within a range in which the lumen 141*b* of the distal member 240 becomes smaller toward a distal end from a proximal end. That is, the first convex portion 244 is formed within a range in which the inner diameter of the distal member 240 of a portion, in which the first convex portion 244 is provided, gradually increases towards the proximal end from the distal end (i.e., the inner diameter of the proximal end of the first convex portion 244 is greater than the inner diameter of the distal end of the first convex portion 244). In addition, the second convex portion 245 is formed within a range in which the inner diameter of the distal member 240 of a portion, in which the second convex portion 245 is provided, is gradually increased toward the proximal end from the distal end. The third convex portion 246 is also formed within a range in which the inner diameter of the distal member 240 of a portion, in which the third convex portion 246 is provided, gradually increases toward the proximal end from the distal end. In other words, for example, if the inner diameter of the distal member 240 at a first position P1 in an extending direction of the distal member 240 is set to L1 and the inner diameter of the distal member 240 at a second position P2 on a proximal side of the first position P1 is set to L2, L1<L2 is satisfied.

According to the distal member 240 of the modification example of the first embodiment illustrated in FIGS. 5(A)-5(C), it is possible to reduce the clearance between the guide wire W1 and the inner surface 240*d* of the distal member 240 when the guide wire W1 protrudes from the distal opening portion 141*a* because the distal member 240 includes the first convex portion 244. Accordingly, it is possible to improve the followability with respect to the guide wire W1 of the distal member 240 (i.e., the ability of the distal member 240 to be moved along the guide wire W2).

It is also possible to reduce the clearance between the guide wire W2 and the inner surface 240*d* of the distal member 240 when the distal member 240 is cut in the first marker portion 142 and the guide wire W2 is inserted into the lumen 141*b* of the distal member 240 because the distal member 240 includes the second convex portion 245. Accordingly, it is possible to improve the followability with respect to the guide wire W2 of the distal member 240 (i.e., the ability of the distal member 240 to be moved along the guide wire W2).

The third convex portion 246 also makes it possible to reduce the clearance between the guide wire W3 and the inner surface 240*d* of the distal member 240 when the distal member 240 is cut in the second marker portion 143 and the guide wire W3 is inserted into the lumen 141*b* of the distal member 240. Accordingly, it is possible to improve the followability with respect to the guide wire W3 of the distal member 240 (i.e., the ability of the distal member 240 to be moved along the guide wire W3).

Second Embodiment

Figure 6:
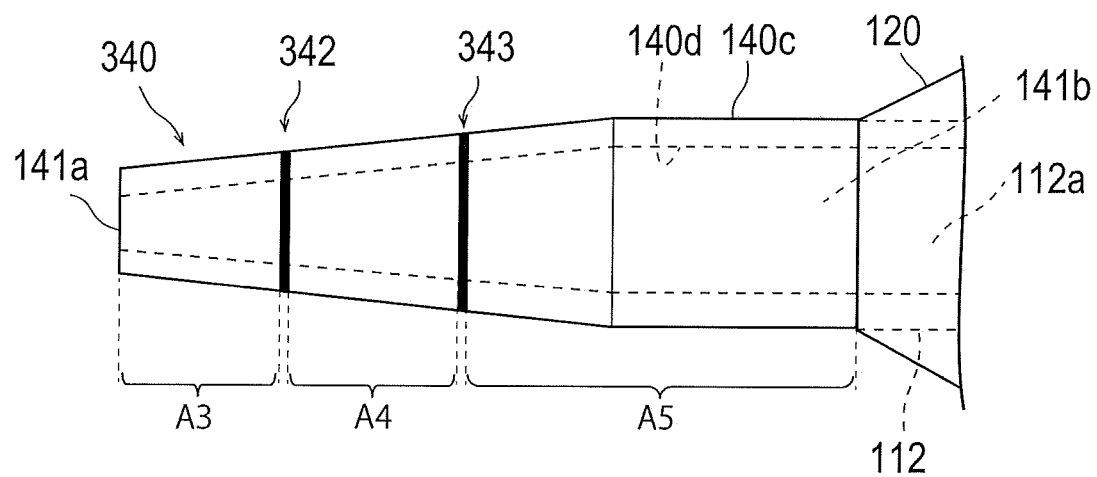
FIG. 6 is an enlarged plan view showing a distal member according to a second embodiment.

FIG. 6 is a view showing a distal member 340 according to a second embodiment. Note that the same reference numerals will be given to the same configurations as those in the first embodiment, and the description of similar aspects of the first embodiment will not be repeated.

The distal member 340 according to the second embodiment is different from the first embodiment in that marker portions 342 and 343 do not have a groove portion and are constituted of a colored line. The distal member 340 according to the second embodiment is described in detail below.

The first marker portion 342 of the embodiment illustrated in FIG. 6 is an annular line extending in a circumferential direction on the outer surface 140*c* of the distal member 340. The first marker portion 342 has a different color than the region A3 of the outer surface 140*c* distal to the first marker portion 342 and a color different than the region A4 of the outer surface 140*c* of the distal member 340 proximal to the first marker portion 342. In other words, the color of the first marker portion 342 is visually distinguishable from the color of the outer surface of the distal member itself.

The second marker portion 343 is positioned proximal to the first marker portion 342. The second marker portion 343 is also an annular line extending in the circumferential direction on the outer surface 140*c* of the distal member 340. The second marker portion 343 has a different color than the region A4 of the outer surface 140*c* of the distal member 340 that is distal to the second marker portion 343 and the region A5 of the outer surface 140*c* that is proximal to the second marker portion 343.

Each of the marker portions 342 and 343 may indicate a position around the circumferential direction and are not necessarily constituted of the annular lines. For example, the marker portion may be constituted of two points which are attached in the circumferential direction and are separated from each other. If the distal member 340 is cut so as to connect the two points to each other (i.e., a cut is made through both points), it is possible to cut the distal member 340 in the circumferential direction. In other words, the visible marker portions 342 and 343 of this application identify a scissile portion (i.e., a portion capable of being cut easily) of the distal member on the outside portion (i.e., when viewed externally) to indicate where the distal member 340 should be cut.

The material of each of the marker portions 342 and 343 is not particularly limited. Examples include a resin kneaded with pigments or an oily colorant such as ink.

According to the distal member 340 of the embodiment illustrated in FIG. 6, each of the marker portions 342 and 343 has a color different from regions on the distal side and the proximal side, which are across the marker portions, on the outer surface 140c of the distal member 340. This makes it is easy for the user to visually recognize each of the marker portions 342 and 343.

As an additional point, since each of the marker portions 342 and 343 includes no groove portion, it is possible to favorably maintain rigidity of the distal member 340.

The above description describes the medical elongated body using the plurality of embodiments and a modification example. However, the medical elongated body is not limited to only the described configurations and can be appropriately changed (e.g., based on the description of the claims).

For example, the medical elongated body disclosed here is not limited to the balloon catheter and also can be applied to a support catheter or the like for introducing a guide wire into a lesion area generated in a biological lumen.

In addition, the distal member 140 has been described as including the tapered portion 140a in which the outer diameter decreases toward the distal end from the proximal end and the flat portion 140b which is continuous to the proximal side of the tapered portion 140a and has a substantially constant outer diameter in the extending direction of the distal member 140. However, the external shape of the distal member is not limited to these examples. For example, the distal member may have a substantially constant outer diameter toward the distal end from the proximal end.

The shape of the lumen is also not particularly limited as long as there is a portion which becomes smaller from the proximal end toward the distal end. For example, the distal member may include a portion with an inner diameter that decreases from the proximal end toward the distal end and a portion possessing a substantially constant inner diameter as described above. However, the distal member may be constituted of, for example, only the portion of which the inner diameter decreases toward the distal end from the proximal end.

The above-described embodiments discuss two marker portions on the outer surface of the distal member. However, the number of marker portions is not particularly limited as long as there are one or more marker portions.

In addition, for example, the groove portion may be made to be easily visually recognized by applying a different color to the groove portion that the color of regions of the outer surface of the distal member on the distal side and the proximal side of the groove portion.

The detailed description above describes a medical elongated body and a method of using a medical elongated body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body comprising:
    a catheter main body comprising a tubular body,
    the tubular body of the catheter main body including a guide wire lumen into which a guide wire is insertable, the tubular body extending in an axial direction and possessing an outer surface;
    the tubular body of the catheter main body possessing a distal portion and comprising a distal member positioned at the distal portion of the tubular body, the distal member comprising a distal end opening that opens to outside the distal member, the distal member possessing an outer surface, an inner surface, an outer diameter, an inner diameter, and a proximal end;
    the distal member comprising a lumen that communicates with the guide wire lumen, the lumen of the distal member being defined by the inner surface of the distal member;
    the inner diameter of the distal member decreasing between the proximal end of the distal member and the distal end opening so that the lumen of the distal member narrows in a direction toward the distal end opening of the distal member;
    a visible marker portion that extends circumferentially on the outer surface of the distal member to indicate a position of the distal member in the axial direction corresponding to a predetermined inner diameter of the distal member, the visible marker portion being visible before the medical elongated body is inserted into a living body, and the visible marker portion being proximal to the distal end opening; and
    the marker portion comprising a groove which is recessed from the outer surface towards the inner surface of the distal member, the groove possessing a width in the axial direction of the tubular body, the width of the groove becoming smaller from the outer surface of the distal member toward the inner surface of the distal member.

2. The medical elongated body according to claim 1, wherein
    the groove of the distal member includes a curved portion, and
    the curved portion is a rounded groove surface of the groove on the outer surface of the distal member.

3. The medical elongated body according to claim 2, wherein
    the groove possesses a deepest point at which the width of the groove is smallest, and
    the curved portion is proximal to the deepest point of the groove.

4. The medical elongated body according to claim 1, wherein the outer surface of the distal member possesses an outer surface color, and the marker portion is a different color than the outer surface color at a region distal to the marker portion and the outer surface color at a region proximal to the marker portion.

5. The medical elongated body according to claim 1, comprising:
    a plurality of the marker portions positioned in axially spaced apart relation to one another on the outer surface of the distal member, and
    the inner surface of the distal member comprising convex portions protruding toward the lumen of the distal member, the convex portions being between adjacent marker portions in the axial direction of the plurality of marker portions.

6. The medical elongated body according to claim 1, comprising:
    a plurality of marker portions on the outer surface of the distal member, the plurality of marker portions including at least a first marker portion and a second marker portion, the first marker portion being axially spaced apart from and distal to the second marker portion on the outer surface of the distal member; and the inner diameter of the distal member at the first marker portion being less than the inner diameter of the distal member at the second marker portion.

7. The medical elongated body according to claim 6, wherein the outer diameter of the outer surface of the distal member at the first marker portion is less than the outer diameter of the distal member at the second marker portion.

8. The medical elongated body according to claim 6, wherein
the inner diameter of the distal member at the first marker portion corresponds to an outer diameter of a first predetermined guide wire that is insertable into the guide wire lumen, and
the inner diameter of the distal member at the second marker portion corresponds to an outer diameter of a second predetermined guide wire that is insertable into the guide wire lumen, the outer diameter of the second predetermined guide wire being greater than the outer diameter of the first predetermined guide wire.

9. A catheter comprising:
a tubular body comprising a guide wire lumen, the tubular body possessing a distal end, a proximal end and an outer surface, the tubular body extending in an axial direction;
the guide wire lumen of the tubular body being configured to receive, at different times, at least a first guide wire and a second guide wire so that the first guide wire and the second guide wire are insertable to pass through the guide wire lumen, the first guide wire possessing an outer diameter and the second guide wire possessing an outer diameter greater than the outer diameter of the first guide wire;
the tubular body comprising a distal member positioned at the distal end of the tubular body, the distal member comprising an open distal end, the distal member possessing an inner surface, an outer diameter, an inner diameter, and a proximal end;
the distal member comprising a lumen that communicates with the guide wire lumen so that the first guide wire and the second guide wire are insertable through the lumen of the distal member to pass beyond the open distal end of the distal member, the lumen of the distal member being surrounded by the inner surface of the distal member;
the inner diameter of the distal member being tapered so that the inner diameter of the distal member decreases between the proximal end of the distal member and the open distal end;
at least two visible grooves extending circumferentially on the outer surface of the distal member, the at least two visible grooves being visible before the catheter is inserted into the living body, the at least two visible grooves comprising a first groove and a second groove that are axially spaced apart from one another so that the first and second grooves axially overlap portions of the distal member possessing different inner diameters;
the first groove being at a position where the inner diameter of the distal member corresponds to the outer diameter of the first guide wire;
the second groove being at a position where the inner diameter of the distal member corresponds to the outer diameter of the second guide wire, the second groove being proximal to the first groove; and
each of the grooves comprising a first edge surface and a second edge surface proximal to the first edge surface, the first edge surface being straight and the second edge surface being rounded.

10. A balloon catheter comprising:
an inner tubular body comprising a guide wire lumen, the tubular body possessing a distal end, a proximal end and an outer surface, the tubular body extending in an axial direction;
an outer tubular body surrounding the inner tubular body, the outer tubular body possessing a distal end and an outer surface, the inner tubular body extending beyond the outer tubular body such that the distal end of the inner tubular body is distal to the distal end of the outer tubular body;
a balloon comprising a distal end and a proximal end, the balloon being inflatable and contractible, the distal end of the balloon being fixed to the outer surface of the inner tubular body and the proximal end of the balloon being fixed to the outer surface of the outer tubular member;
the guide wire lumen of the inner tubular body being configured to receive, at different times, at least a first guide wire and a second guide wire so that the first guide wire and the second guide wire are insertable to pass through the guide wire lumen, the first guide wire possessing an outer diameter and the second guide wire possessing an outer diameter greater than the outer diameter of the first guide wire;
the inner tubular body comprising a distal member positioned at the distal end of the inner tubular body, the distal member comprising an open distal end, the distal member possessing an inner surface, an outer diameter, an inner diameter, and a proximal end;
the distal member comprising a lumen that communicates with the guide wire lumen so that the first guide wire and the second guide wire are insertable through the lumen of the distal member to pass beyond the open distal end of the distal member, the lumen of the distal member being surrounded by the inner surface of the distal member;
the inner diameter of the distal member being tapered so that the inner diameter of the distal member decreases between the proximal end of the distal member and the open distal end;
at least two visible markers extending circumferentially on the outer surface of the distal member, the at least two visible markers being visible before the catheter is inserted into the living body, the at least two visible markers comprising a first marker and a second marker that are axially spaced apart from one another so that the first and second markers axially overlap portions of the distal member possessing different inner diameters;
the first marker being at a position where the inner diameter of the distal member corresponds to the outer diameter of the first guide wire; and
the second marker being at a position where the inner diameter of the distal member corresponds to the outer diameter of the second guide wire, the second marker being proximal to the first marker.

11. The balloon catheter according to claim 10, wherein the at least two visible markers are grooves formed into the outer surface of the distal member.

12. The balloon catheter according to claim 11, wherein the grooves possess a V-shaped cross sectional shape.

13. The balloon catheter according to claim 11, wherein each of the grooves comprises a first edge surface and a second edge surface proximal to the first edge surface, the first edge surface being straight and the second edge surface being rounded.

* * * * *